(12) United States Patent
Ootsuka et al.

(10) Patent No.: US 9,409,843 B2
(45) Date of Patent: Aug. 9, 2016

(54) METHOD FOR PRODUCING 1,1,1,5,5,5-HEXAFLUOROACETYLACETONE

(71) Applicant: Central Glass Company, Limited, Ube-shi, Yamaguchi (JP)

(72) Inventors: Takashi Ootsuka, Kawagoe (JP); Takashi Masuda, Kawagoe (JP); Akihiro Ishii, Kawagoe (JP); Mari Imamura, Kawagoe (JP); Shunsuke Mimura, Kawagoe (JP); Masato Kimura, Ube (JP); Hiroshi Minesaki, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/783,706

(22) PCT Filed: Apr. 2, 2014

(86) PCT No.: PCT/JP2014/059731
§ 371 (c)(1),
(2) Date: Oct. 9, 2015

(87) PCT Pub. No.: WO2014/168056
PCT Pub. Date: Oct. 16, 2014

(65) Prior Publication Data
US 2016/0075626 A1   Mar. 17, 2016

(30) Foreign Application Priority Data

Apr. 11, 2013 (JP) ................................ 2013-082589
Mar. 27, 2014 (JP) ................................ 2014-065450

(51) Int. Cl.
| | | |
|---|---|---|
| *C07C 45/26* | (2006.01) | |
| *C07C 33/00* | (2006.01) | |
| *C07C 43/00* | (2006.01) | |
| *C07C 49/167* | (2006.01) | |
| *C07C 49/227* | (2006.01) | |
| *C07C 45/45* | (2006.01) | |
| *C07C 33/42* | (2006.01) | |
| *C07C 43/178* | (2006.01) | |

(52) U.S. Cl.
CPC .............. *C07C 45/26* (2013.01); *C07C 33/426* (2013.01); *C07C 43/1786* (2013.01); *C07C 45/45* (2013.01); *C07C 49/167* (2013.01); *C07C 49/227* (2013.01)

(58) Field of Classification Search
CPC .... C07C 45/26; C07C 33/426; C07C 43/1786
USPC ......................................... 568/407, 674, 843
See application file for complete search history.

(56) References Cited

U.S. PATENT DOCUMENTS

| | | | |
|---|---|---|---|
| 6,037,482 | A | 3/2000 | Schulz et al. |
| 6,384,286 | B1 | 5/2002 | Komata et al. |
| 6,392,101 | B2 | 5/2002 | Komata et al. |
| 6,548,712 | B2 | 4/2003 | Komata et al. |
| 2001/0034462 | A1 | 10/2001 | Komata et al. |
| 2002/0010373 | A1 | 1/2002 | Komata et al. |
| 2002/0022748 | A1 | 2/2002 | Komata et al. |

FOREIGN PATENT DOCUMENTS

| | | |
|---|---|---|
| CN | 102260151 A | 11/2011 |
| JP | 63-77834 A | 4/1988 |
| JP | 2000-502077 A | 2/2000 |
| JP | 2001-187760 A | 7/2001 |
| JP | 2001-261607 A | 9/2001 |
| JP | 2001-354610 A | 12/2001 |
| JP | 2004-2466 A | 1/2004 |
| WO | WO 2008/132964 A1 | 11/2008 |

OTHER PUBLICATIONS

International Search Report (PCT/ISA/210) issued in PCT Application No. PCT/JP2014/059731 dated Jul. 8, 2014, with English translation (four (4) pages).
Japanese-language Written Opinion (PCT/ISA/237) issued in PCT Application No. PCT/JP2014/059731 dated Jul. 8, 2014 (four (4) pages).
H. Gilman et al., Organic Compounds of Uranium. I. 1,3-Dicarbonyl Chelates, J. Am. Chem. Soc., 1956, vol. 78, pp. 2790-2792.
Sabiha Tajammal et al., Fluorinated Acetylenes Part 7 [1] Preparation and Some Reactions of 4,4,4-Trifluorobut-2-YNOIC Acid and 1-Phenyl-4,4,4-Trifluorobut-2-YN-1-OL, Journal of Fluorine Chemistry,1989, vol. 47, pp. 45-57.
Michael G. Barlow et al., Fluorinated Acetylenes. Part 10.[1] Cycloadditions of α,α-Bis(3,3,3-trifluoropropynyl)benzyl Benzoate and 1,1-Bis(3,3,3-trifluoro-propynyl) ethyl Ethanoate with Furan and Cyclopentadiene[2], J. Chem. Soc. Perkin Trans., 1992, pp. 2485-2494.
Lakhdar Sibous et al., Fluorinated acetylenes. Part 8 [1]. Preparation and some reactions of 5,5,5-trifluoropent-3-yn-2-ol, 5,5,5-trifluoro-1phenylpent-3-yn-2-ol and the derived ester, 2-acetoxy-5,5,5-trifluoropent-3-yne, Journal of Fluorine Chemistry, 1993, vol. 62, pp. 39-49.
Takashi Yamazaki et al., Modified Preparation Method of Trifluoromethylated Propargylic Alcohols and Its Application to Chiral 2,6-Dideoxy-6,6,6-trifluorosugars, J. Org. Chem., 1995, vol. 60, pp. 6046-6056.
Ei-ichi Negishi et al., Michael and Anti-Michael Additions to Benzoyl(trifluoromethyl)acetylene, J. Org. Chem., 1986, vol. 51, pp. 4082-4083.

(Continued)

*Primary Examiner* — Sikarl Witherspoon
(74) *Attorney, Agent, or Firm* — Crowell & Moring LLP

(57) ABSTRACT

A production method of a 1,1,1,5,5,5-hexafluoroacetylacetone hydrate according to the present invention includes: step 1: obtaining a reaction mixture that contains at least 1,1,1,5,5,5-hexafluoro-3-pentyn-2-one or an equivalent thereof by reaction of a 3,3,3-trifluoropropynyl metal with a trifluoroacetate; and step 2: forming the 1,1,1,5,5,5-hexafluoroacetylacetone hydrate by contact of the reaction mixture obtained in the step 1 with water in the presence of an acid. It is possible to produce 1,1,1,5,5,5-hexafluoroacetylacetone by dehydration of the thus-formed hydrate. Thus, the production method according to the present invention is industrially applicable.

14 Claims, No Drawings

(56) References Cited

OTHER PUBLICATIONS

Valerie Martin et al., Anti-Michael Additions and Fluoride Ion Elimination on β,β-Bis(trifluoromethyl)acrylic Esters. Preparation of α-Substituted Acetic Acid Esters, J. Org. Chem., 1992, vol. 57, pp. 5530-5532.

M. N. Bobrovuikov et al., Synthesis of Trifluoromethyl- and Pentafluorophenylalkenynes, Russian Journal of Organic Chemistry, 1993, vol. 29, No. 9, pp. 1445-1449.

Alan K. Brisdon et al., Hydrofluorocarbon 245fa : a versatile new synthon in alkyne chemistry, Chem Commun, 2002, pp. 2420-2421.

Theodora W. Greene et al., Protective Groups in Organic Synthesis, Third Edition, 1999, John Wiley & Sons, Inc. (twenty eight (28) pages).

R. Linn Belford et al., Influence of Fluorine Substitution on the Properties of Metal Chelate Compounds-I, J. Inorganic and Nuclear Chemistry, 1956, vol. 2, pp. 11-31.

Yanchang Shen et al., A Facile Synthesis of Symmetrically Substituted Perfluoro-α,β-ynones, Synthesis, 1984, No. 11, pp. 924-926.

Yuji Hanzawa et al., Enantioselective Reduction of Fluoroalkyl Alkynyl Ketones: Enormous Electronic Effect of the Trifluoromethyl Group, Chem. Pharm. Bull. 1987, vol. 35, No. 6, pp. 2609-2612.

Xavier Creary, Reaction of Organometallic Reagents with Ethyl Trifluoroacetate and Diethyl Oxalate. Formation of Trifluoromethyl Keytones and α-Keto Esters via Stable Tetrahedral Adducts, J. Org. Chem, 1987, vol. 52, pp. 5026-5030.

Chinese Office Action issued in counterpart Chinese Application No. 201480020532.X dated Mar. 31, 2016 (seven (7) pages).

Xavier Creary, "Reaction of Organometallic Reagents with Ethyl Frifluoroacetate and Diethyl Oxalate. Formation of Trifluoromethyl Ketones and α-Keto Esters via Stable Tetrahedral Adducts", J. Org. Chem. 1987, vol. 52, No. 22, pp. 5026-5030.

METHOD FOR PRODUCING 1,1,1,5,5,5-HEXAFLUOROACETYLACETONE

FIELD OF THE INVENTION

The present invention relates to a method for producing 1,1,1,5,5,5-hexafluoroacetylacetone.

BACKGROUND ART

As typical production methods of 1,1,1,5,5,5-hexafluoroacetylacetone, there are known; reaction of trifluoroacetone and trifluoroacetate (Non-Patent Publication 1); and reaction of trifluoroacetoacetate and trifluoroacetic anhydride (Patent Document 1).

On the other hand, there are reports about reaction of trifluoropropynyl metal compounds (e.g. $CF_3C{\equiv}CLi$) with various electrophilic reagents (Non-Patent Documents 2 to 5). There are also reports about reaction of trifluoromethyl-containing carbon-carbon multiple bond compounds with various nucleophilic reagents (Non-Patent Documents 4, 6 and 7).

PRIOR ART DOCUMENTS

Patent Documents

Patent Document 1: Chinese Patent Application Publication No. 102260151

Non-Patent Documents

Non-Patent Document 1: J. Am. Chem. Soc. (U.S.), 1956, vol. 78, p. 2790-2792
Non-Patent Document 2: J. Fluorine Chem. (Holland), 1990, vol. 47, p. 45-57
Non-Patent Document 3: J. Chem. Soc. Perkin Trans. 1, (U.K.), 1992, p. 2485-2494
Non-Patent Document 4: J. Fluorine Chem. (Holland), 1993, vol. 62, p. 39-49
Non-Patent Document 5: J. Org. Chem. (U.S.), 1995, vol. 60, p. 6046-6056
Non-Patent Document 6: J. Org. Chem. (U.S.), 1986, vol. 51, p. 4082-4083
Non-Patent Document 7: J. Org. Chem. (U.S.), 1992, vol. 57, p. 5530-5532

SUMMARY OF THE INVENTION

Problems to be Solved by the Invention

In the case of producing 1,1,1,5,5,5-hexafluoroacetylacetone as disclosed by Non-Patent Document 1, it is necessary to utilize expensive raw substrate material (more specifically, trifluoroacetone). The production method of Non-Patent Document 1 is thus difficult to industrially adopt in view of the ease of availability of the raw substrate material.

The production method of Patent Document 1 does not utilize trifluoroacetone as raw substrate material and has improved cost-competitiveness as compared to the production method of Non-Patent Document 1. However, there has been a strong demand to develop a more industrially easily applicable production method.

It is accordingly an object of the present invention to provide an industrially easily applicable production method of 1,1,1,5,5,5-hexafluoroacetylacetone.

Means for Solving the Problems

In view of the above circumstances, the present inventors have made extensive researches and resultantly found that: it is possible to form a 1,1,1,5,5,5-hexafluoroacetylacetone hydrate by reacting a 3,3,3-trifluoropropynyl metal with a trifluoroacetate and then bringing the resulting reaction mixture (A), in which at least 1,1,1,5,5,5-hexafluoro-3-pentyn-2-one or an equivalent thereof is contained, into contact with water in the presence of an acid; and it is possible to produce 1,1,1,5,5,5-hexafluoroacetylacetone by dehydration of the thus-formed hydrate.

Namely, the present invention includes the following inventive aspects 1 to 14.

[Inventive Aspect 1]

A method for producing a 1,1,1,5,5,5-hexafluoroacetylacetone hydrate of the general formula [3]:

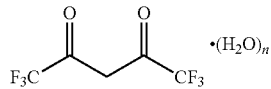

where n represents a positive integer,
the method comprising:
step 1: obtaining a reaction mixture (A) that contains at least 1,1,1,5,5,5-hexafluoro-3-pentyn-2-one or an equivalent thereof by reaction of a 3,3,3-trifluoropropynyl metal of the general formula [1] with a trifluoroacetate of the general formula [2]:

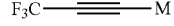

where M represents a lithium atom or a halogenated magnesium group (MgX); and X represents a chlorine atom, a bromine atom or an iodine atom;

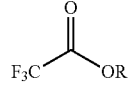

where R represents an alkyl group; and
step 2: forming the 1,1,1,5,5,5-hexafluoroacetylacetone hydrate of the general formula [3] by contact of the reaction mixture (A) obtained in the step 1 with water in the presence of an acid.

[Inventive Aspect 2]

The method according to Inventive Aspect 1, further comprising: purifying the 1,1,1,5,5,5-hexafluoroacetylacetone hydrate formed in the step 2.

[Inventive Aspect 3]

The method according to Inventive Aspect 2, wherein the reaction of the step 1 is performed with the use of a reaction solvent.

[Inventive Aspect 4]

The method according to Inventive Aspect 3, further comprising: recycling at least one of the reaction solvent and raw substrate material separated from the 1,1,1,5,5,5-hexafluoroacetylacetone hydrate.

[Inventive Aspect 5]

The method according to any one of Inventive Aspects 1 to 4, wherein the equivalent of the 1,1,1,5,5,5-hexafluoro-3-pentyn-2-one is a 1,1,1,5,5,5-hexafluoro-3-pentyn-2-one metal hemiketal of the general formula [5]:

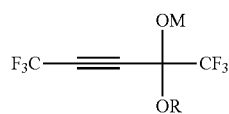

[5]

where M is a lithium atom or a halogenated magnesium group (MgX); X represents a chlorine atom, a bromine atom or an iodine atom; and R represents an alkyl group.

[Inventive Aspect 6]

The method according to any one of Inventive Aspects 1 to 4, wherein the equivalent of the 1,1,1,5,5,5-hexafluoro-3-pentyn-2-one is a 1,1,1,5,5,5-hexafluoro-3-pentyn-2-one hydrate or alkyl hemiketal of the general formula [6]:

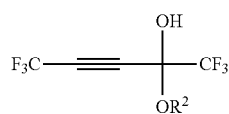

[6]

where $R^2$ represents a hydrogen atom or an alkyl group.

[Inventive Aspect 7]

The method according to any one of Inventive Aspects 1 to 6, wherein M of the 3,3,3-trifluoropropyl metal of the general formula [1] is a lithium atom.

[Inventive Aspect 8]

The method according to any one of Inventive Aspects 1 to 7, wherein the acid is sulfuric acid.

[Inventive Aspect 9]

A method for producing 1,1,1,5,5,5-hexafluoroacetylacetone of the formula [4]:

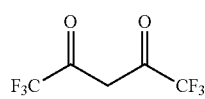

[4]

the method comprising:

producing a 1,1,1,5,5,5-hexafluoroacetylacetone hydrate by the method according to any one of Inventive Aspects 1 to 8; and dehydrating the 1,1,1,5,5,5-hexafluoroacetylacetone hydrate.

[Inventive Aspect 10]

A 1,1,1,5,5,5-hexafluoro-3-pentyn-2-one metal hemiketal of the general formula [5]:

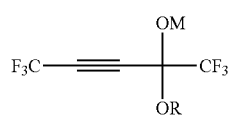

[5]

where M represents a lithium atom or a halogenated magnesium group (MgX); X represents a chlorine atom, a bromine atom or an iodine atom; and R represents an alkyl group.

[Inventive Aspect 11]

A 1,1,5,5,5-hexafluoro-3-pentyn-2-one hydrate or alkyl hemiketal of the general formula [6]:

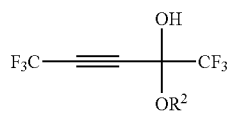

[6]

where $R^2$ represents a hydrogen atom or an alkyl group.

[Inventive Aspect 12]

A method for producing a 1,1,1,5,5,5-hexafluoroacetylacetone hydrate of the general formula [3]:

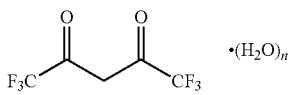

[3]

where n represents a positive integer, the method comprising:

step 1': obtaining a preparation solution (B) by reaction of 3,3,3-trifluoropropyne of the formula [7] with an organic lithium reagent or Grignard reagent of the general formula [8] in a preparation solvent, and then, obtaining a reaction mixture (C) by reaction of the preparation solution (B) with a trifluoroacetate of the general formula [2]:

[7]

[8]

where $R^3$ represents a $C_1$-$C_8$ straight or branched or $C_3$-$C_8$ cyclic alkyl group; M represents a lithium atom or a halogenated magnesium group (MgX); and X represents a chlorine atom, a bromine atom or an iodine atom;

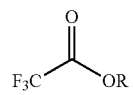

[2]

where R represents an alkyl group; and step 2': forming the 1,1,1,5,55-hexafluoroacetylacetone hydrate of the general formula [3] by contact of the reaction mixture (C) obtained in the step 1' with water in the presence of an acid.

[Inventive Aspect 13]

The method according to Inventive Aspect 12, further comprising: purifying the 1,1,1,5,5,5-hexafluoroacetylacetone hydrate formed in the step 2' to a higher purity level.

[Inventive Aspect 14]

The method according to Inventive Aspect 13, further comprising: purifying and recycling at least one of the preparation solution and raw substrate material separated from the 1,1,1,5,5,5-hexafluoroacetylacetone hydrate.

There has been no report made about the formation of a trifluoromethyl-containing ynone ($CF_3C{\equiv}CCOR^1$ where $R^1$ represents an alkyl group or an aryl group) or an equivalent thereof by a 3,3,3-trifluoropropynyl metal with an ester as an electrophilic reagent. For example, 3,3,3-trifluoropropynyl lithium favorably reacts with an aldehyde or an ketone to form a target product at a high yield. By contrast, 3,3,3-trifluoropropynyl lithium reacts with an ester to merely form a complicated mixture (see Non-Patent Document 5). As a matter of course, there has been no report made on the reaction of a trifluoroacetate with an electrophilic reagent as disclosed by the present invention. Although there occurs hydration of a triple bond of 1,1,1,5,5,5-hexafluoro-3-pentyn-2-one ($CF_3C{\equiv}CCOCF_3$) or its equivalent in the present invention, it has been uncertain whether a hydroxyl group can be introduced into 4-position as desired. For example, the reactions of trifluoromethyl-containing carbon-carbon multiple bond compounds ($CF_3C{\equiv}CCH(OAc)Me$, $CF_3C{\equiv}CCOPh$, $(CF_3)_2C{=}CHCO_2Et$ where Ac represents an acetyl group; Me represents a methyl group; Ph represents a phenyl group; and Et represents an ethyl group) and various nucleophilic reagents are reported in Non-Patent Documents 4, 6 and 7. In these reactions, however, conjugate adducts having a trifluoromethyl group as an electron attracting group are obtained as main products. The positional selectivity of the reactions of Non-Patent Documents 4, 6 and 7 is opposite to that desired in the present invention.

One of the raw substrate compounds of the present invention, 3,3,3-trifluoropropynyl metal, can be easily derived from 3,3,3-trifluoropropyne, which is readily available in large scale. The other raw substrate compound of the present invention, trifluoroacetate, is also readily available in large scale. The production method of the present invention is thus industrially easily applicable for production of 1,1,1,5,5,5-hexafluoroacetylacetone.

DETAILED DESCRIPTION OF THE INVENTION

The production method of 1,1,1,5,5,5-hexafluoroacetylacetone according to the present invention will be described in detail below. It should be understood that: the scope of the present invention is not limited to the following embodiments; and various changes and modifications of the following embodiments can be made as appropriate without impairing the scope of the present invention. All of the publications cited in the present specification (such as prior art documents including patent documents and non-patent documents) are herein incorporated by reference. In the following description, the structures of the general formulas [1] to [3], [5], [6] and [8] and the structures of the formulas [4] and [7] are as defined above.

In the present invention, the 1,1,1,5,5,5-hexafluoroacetone hydrate of the general formula [3] is formed by reacting the 3,3,3-trifluoropropynyl metal of the general formula [1] with the trifluoroacetate of the general formula [2], and then, bringing the resulting reaction mixture (A) into contact with the water in the presence of the acid. The 1,1,1,5,5,5-hexafluoroacetone of the formula [4] is produced by dehydration of the thus-formed hydrate. The reaction mixture (A) contains at least 1,1,1,5,5,5-hexafluoro-3-pentyn-2-one or its equivalent. There is no particular restriction on the equivalent of 1,1,1,5,5,5-hexafluoro-3-pentyn-2-one as long as the equivalent is capable of being converted to the 1,1,1,5,5,5-hexafluoroacetone hydrate of the general formula [3] by the step 2 (i.e. by contact with the water in the presence of the acid) as will be explained later. The equivalent of 1,1,1,5,5,5-hexafluoro-3-pentyn-2-one can be in metal hemiketal form of the general formula [5] or in hydrate or alkyl hemiketal form of the general formula [6]. Although the equivalent is not limited to limited to these compounds, each of these equivalent compounds is very important as the equivalent of 1,1,1,5,5,5-hexafluoro-3-pentyn-2-one and serves as a very important precursor of 1,1,1,5,5,5-hexafluoroacetone or its hydrate.

[Step 1]

The step 1 will be now explained below. In the step 1, the reaction mixture (A), in which at least 1,1,1,5,5,5-hexafluoro-3-pentyn-2-one or its equivalent is contained, is obtained by reaction of the 3,3,3-trifluoropropynyl metal of the general formula [1] with the trifluoroacetate of the general formula [2].

Herein, the following terms have the following meanings. The step 1a refers to the case where the 1,1,1,5,5,5-hexafluoro-3-pentyn-2-one metal hemiketal is explicitly contained as the equivalent of 1,1,1,5,5,5-hexafluoro-3-pentyn-2-one in the reaction mixture (A). The step 1b refers to the case where the 1,1,1,5,5,5-hexafluoro-3-pentyn-2-one hydrate or alkyl hemiketal is explicitly contained as the equivalent of 1,1,1,5,5,5-hexafluoro-3-pentyn-2-one in the reaction mixture (A). The step 1' refers to the case where the 3,3,3-trifluoropropynyl metal is provided as the preparation solution (B) (sometimes simply called "preparation solution") as will be explained later. The reaction mixture (C) refers to that obtained in the step 1'. In the present specification, the step 1a, the step 1b and the step 1' are regarded as embodiments of the step 1 unless otherwise clearly distinguished.

In the 3,3,3-trifluoropropynyl metal of the general formula [1] used in the step 1, M represents a lithium atom or a halogenated magnesium group (MgX); and X represents a chlorine atom, a bromine atom or an iodine atom. In order for the desired reaction to smoothly proceeds in the step 1, a lithium atom, a magnesium chloride group (MgCl) and a magnesium bromide group (MgBr) are preferred. More preferred is a lithium atom.

The 3,3,3-trifluoropropynyl metal can be derived from 3,3,3-trifluoropropyne with reference to Non-Patent Publications 2 to 4, Russian Journal of Organic Chemistry (Russia), 1993, vol. 29, p. 1445-1449 and the like. More specifically, it is feasible to prepare the 3,3,3-trifluoropropynyl metal of the general formula [1] at a high yield (as the preparation solution (B)) by reacting the 3,3,3-trifluoropropyne with the organic lithium reagent or Grignard reagent of the general formula [8] in the preparation solvent for 12 hours or less at $-150°$ C. to $+50°$ C. In this preparation operation, it is convenient to use various commercially-available concentration-adjusted solution of the organic lithium reagent or Grignard reagent. It suffices to use the 3,3,3-trifluoropropyne in an amount of 0.7 mol or more per 1 mol of the organic lithium reagent or Grignard reagent. The amount of the 3,3,3-trifluoropropyne used is preferably 0.8 to 1.6 mol, more preferably 0.9 to 1.3 mol, per 1 mol of the organic lithium reagent or Grignard reagent. The amount of the preparation solution used is adjusted in consideration of the amount of the reaction solvent used in the step 1. Alternatively, the 3,3,3-trifluoropropynyl metal can be derived from 2-bromo-3,3,3-trifluoropropene or 1,1,1,3,3-pentafluoropropane with reference to Non-Patent Document 5, Chem. Commun. (U.K.), 2002, p. 2420-2421 and the like. The preparation of the 3,3,3-trifluoropropynyl metal is not however limited to these processes.

The 3,3,3-trifluoropropyne is readily available in large scale by a production method as disclosed in International Publication No. WO 2008/132964 etc. As compared to trifluoroacetone and trifluoroacetoacetate used in the background art, the 3,3,3-trifluoropropyne is industrially easily applicable as a nucleophilic reagent ($CF_3COCH_2^-$ equivalent) for the production of the 1,1,1,5,5,5-hexafluoroacetone. It is thus a preferred embodiment of the present invention to derive the 3,3,3-trifluoropropynyl metal from the 3,3,3-trifluoropropyne.

In the step 1, an impurity may be contained in the 3,3,3-trifluoropropynyl metal as long as the impurity does not interfere with the present step 1 and the subsequent step 2. The 3,3,3-trifluoropropynyl metal obtained by any process can be used in the step 1. It is feasible to use a purified product of the 3,3,3-trifluoropropynyl metal in the reaction. However, the 3,3,3-trifluoropropynyl metal is unstable against heat, moisture, oxygen etc. It is thus preferable that the solution containing the 3,3,3-trifluoropropynyl metal as a product (i.e. preparation reaction) is directly used in the reaction. The solvent of this solution (i.e. preparation solvent) is preferably the same as the reaction solvent used in the step 1.

Depending on the process for preparation of the 3,3,3-trifluoropropynyl metal as the raw material, lithium hydride, lithium halide (fluoride, chloride, bromide or iodide), magnesium halide (fluoride, chloride, bromide or iodide), methane, ethane, propane, n-butane, benzene, diisopropylamine, hexamethyldisilazane, 2,2,6,6-tetramethylpiperidine or the like may be contained in the preparation solution. There is however no need to remove such an impurity compound. The reaction of the step 1 can be performed in the presence of the impurity compound. Naturally, it is feasible to perform the reaction with the intentional addition of the impurity compound.

In the present invention, an aggregate of the 3,3,3-trifluoropropynyl metal ($CF_3C\equiv CM$), a complex of the 3,3,3-trifluoropropynyl metal with any compound or solvent mixed in the preparation solution and an aggregate of such a complex are regarded as embodiments of the 3,3,3-trifluoropropynyl metal of the general formula [1].

In the trifluoroacetate of the general formula [2] used in the step 1, R represents an alkyl group. The alkyl group has a $C_1$-$C_{12}$ straight- or branched chain structure or a $C_3$-$C_{12}$ cyclic structure. Among others, $C_1$-$C_4$ alkyl groups are preferred. Particularly preferred are a methyl group and an ethyl group. The alkyl group may have a substituent that does not exert a substantial influence on the desired reaction. Such a substituted alkyl group is also included in the claimed alkyl group R of the trifluoroacetate of the general formula [2]. As the substituent, there can be used a halogen atom such as fluorine or chlorine, a $C_1$-$C_6$ alkoxy group such as methoxy or ethoxy etc.

It suffices to use the trifluoroacetate of the general formula [2] in an amount of 0.7 mol or more per 1 mol of the 3,3,3-trifluoropropynyl metal of the general formula [1]. The amount of the trifluoroacetate used is preferably 0.8 to 5 mol, more preferably 0.9 to 3 mol, per 1 mol of the 3,3,3-trifluoropropynyl metal.

In the step 1, the desired reaction of the 3,3,3-trifluoropropynyl metal of the general formula [1] and the trifluoroacetate of the general formula [2] may proceed favorably with the addition of an additive such as a zinc halide (fluoride, chloride, bromide or iodide), a diethyl ether complex of boron trifluoride, 12-crown-4, polyethylene glycol, hexamethylphosphoric triamide (abbreviated as "HMPA") or N,N,N',N'-tetramethylethylenediamine (abbreviated as "TMEDA"). As a matter of course, the above additive is not necessarily required in the case where the suitable reaction conditions are adopted in the present invention.

The step 1 can be performed in a batch reaction system or a flow reaction system. Naturally, it is possible to continuously perform the preparation of the 3,3,3-trifluoropropynyl metal and the reaction of the 3,3,3-trifluoropropynyl metal and the trifluoroacetate in a flow reaction system.

The reaction solvent may be used in the step 1. Examples of the reaction solvent are: aliphatic hydrocarbon solvents such as n-pentane, n-hexane, cyclohexane and n-heptane; aromatic hydrocarbon solvents such as benzene, toluene, xylene, cumene and mesitylene; ether solvents such as diethyl ether, tetrahydrofuran, 1,2-dimethoxyethane, 1,4-dioxane, tert-butyl methyl ether, e-methyltetrahydrofuran, diethoxymethane, diisopropyl ether, diethylene glycol dimethyl ether, anisole, di-n-butyl ether and diethylene glycol dibutyl ether; amide solvents such as N,N-dimethylformamide, N,N-dimethylacetamide, N-methyl-2-pyrrolidone and 1,3-dimethyl-2-imidazolidinone; and dimethylsulfoxide. Among others, the aliphatic hydrocarbon solvents, aromatic hydrocarbon solvents and ether solvents are preferred. Particularly preferred are the ether solvents. These reaction solvents can be used solely or in combination thereof.

In the step 1, it suffices to use the reaction solvent in an amount of 0.05 L (where L designates liter; the same applies to the following) per 1 mol of the 3,3,3-trifluoropropynyl metal of the general formula [1]. The amount of the reaction solvent used is preferably 0.1 to 30 L, more preferably 0.2 to 20 L, per 1 mol of the 3,3,3-trifluoropropynyl metal. As mentioned above, the amount of the amount of the reaction solvent used includes the solvent of the solution of the 3,3,3-trifluoropropynyl metal.

It suffices in the step 1 that the reaction temperature is +75° C. or lower. The reaction temperature is preferably in a range of +50° C. to −100° C., more preferably +25° C. to −75° C., still more preferably 0° C. to −50° C. Herein, the reaction temperature refers to the temperature of the reaction of the 3,3,3-trifluoropropynyl metal of the general formula [1] and the trifluoroacetate of the general formula [2] rather than the temperature of the preparation of the 3,3,3-trifluoropropynyl metal.

Further, it suffices in the step 1 that the reaction time is 48 hours or less. The reaction time is varied depending on the raw substrate material and the reaction conditions. It is thus preferable to monitor the progress of the reaction by analytical means such as gas chromatography, liquid chromatography or nuclear magnetic resonance, and then, determine the point at which there is seen almost no decrease of the raw substrate material as the end of the reaction.

After the reaction of the step 1, the reaction mixture (A) is obtained by ordinary post-treatment operation for organic synthesis. The reaction mixture (A) contains at least 1,1,1,5,5,5-hexafluoro-3-pentyn-2-one ($CF_3C\equiv CCOCF_3$) or its equivalent as reaction intermediate. The equivalent is in metal hemiketal form, hydrate or alkyl hemiketal form or the like. The reaction solvent used in the step 1, by-product (such as corresponding metal alkoxide: ROM) and unreacted raw material may also be contained in the reaction mixture. In the case where the reaction solvent, by-product and unreacted raw material are contained in the reaction mixture, it is feasible to, after forming the 1,1,1,5,5,5-hexafluoroacetylacetone hydrate in the step 2, recover the reaction solvent, by-product and unreacted raw material by separation/purification of the 1,1,1,5,5,5-hexafluoroacetylacetone hydrate, and then, purify and recycle the recovered reaction solvent, by-product or unreacted raw material.

The 1,1,1,5,5,5-hexafluoro-3-pentyn-2-one or its equivalent formed as the reaction mixture (A) can be used, with or without isolation, in the subsequent step. Either of these cases is included in the claimed reaction mixture (A).

[Step 2]

Next, the step 2 will be explained. In the step 2, the 1,1,1,5,5,5-hexafluoroacetylacetone hydrate of the general formula [3] is formed by contact of the reaction mixture (A) obtained in the step 1 with the water in the presence of the acid.

Herein, the following terms have the following meanings. The step 2a refers to the case where the 1,1,1,5,5,5-hexafluoro-3-pentyn-2-one metal hemiketal is explicitly contained as the equivalent of 1,1,1,5,5,5-hexafluoro-3-pentyn-2-one in the reaction mixture (A). The step 2b refers to the case where the 1,1,1,5,5,5-hexafluoro-3-pentyn-2-one hydrate or alkyl hemiketal is explicitly contained as the equivalent of 1,1,1,5,5,5-hexafluoro-3-pentyn-2-one in the reaction mixture (A). The step 2' refers to the case where the reaction mixture (C) obtained in the step 1' is used in place of the reaction mixture (A) obtained in the step 1. In the present specification, the step 2a, the step 2b and the step 2' are regarded as embodiments of the step 2 unless otherwise clearly distinguished.

It is convenient and industrially practical to perform the step 2 on the reaction completed solution, as it is by the reaction of the 3,3,3-trifluoropropynyl metal of the general formula [1] and the trifluoroacetate of the general formula [2], without any treatment.

The structural formula of 1,1,1,5,5,5-hexafluoro-3-pentyn-2-one is as follows.

The 1,1,1,5,5,5-hexafluoro-3-pentyn-2-one metal hemiketal of the general formula [5] is a specific example of the equivalent of 1,1,1,5,5,5-hexafluoro-3-pentyn-2-one.

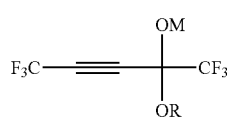

[5]

In the general formula [5], M represents a lithium atom or a halogenated magnesium group (MgX); X represents a chlorine atom, a bromine atom or an iodine atom; and R represents an alkyl group. Herein, M and R are derived from and are the same as those of the 3,3,3-trifluoropropynyl metal of the general formula [1] and the trifluoroacetate of the general formula [2], respectively.

For example, 1,1,1,5,5,5-hexafluoro-3-pentyn-2-one trimethylsilyl ethyl ketal of the following formula can be obtained at a high yield by reacting 3,3,3-trifluoropropynyl lithium with ethyl trifluoroacetate, and then, directly reacting the resulting reaction mixture solution with trimethylsilyl chloride as mentioned later in Example 2.

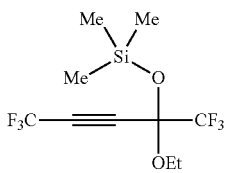

In the formula, Me represents a methyl group; and Et represents an ethyl group. It is apparent in this example that the 1,1,1,5,5,5-hexafluoro-3-pentyn-2-one metal hemiketal of the general formula [5] (M: lithium atom, R: ethyl group) is present in the reaction mixture solution.

The equivalent of 1,1,1,5,5,5-hexafluoro-3-pentyn-2-one contained in the reaction mixture (A) is not limited to the 1,1,1,5,5,5-hexafluoro-3-pentyn-2-one metal hemiketal of the general formula [5]. The equivalent of 1,1,1,5,5,5-hexafluoro-3-pentyn-2-one contained in the reaction mixture (A) can be in any form capable of being converted to the 1,1,1,5,5,5-hexafluoroacetone hydrate of the general formula [3]. The 1,1,1,5,5,5-hexafluoro-3-pentyn-2-one hydrate or alkyl hemiketal of the general formula [6] is such an example of the equivalent of 1,1,1,5,5,5-hexafluoro-3-pentyn-2-one.

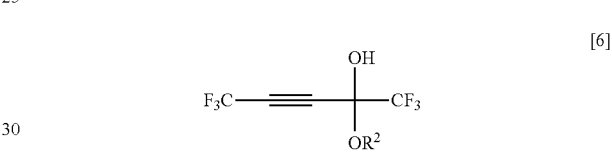

[6]

In the general formula [6], $R^2$ represents a hydrogen atom or an alkyl group. Herein, $R^2$ is derived from and is the same as R of the trifluoroacetate of the general formula [2].

There is no particular restriction on the kind of the acid used in the step 2. Examples of the acid are: inorganic acids such as hydrogen chloride, hydrogen bromide, hydrogen iodide, perchloric acid, sulfuric acid, nitric acid and fluorosulfonic acid; and organic acids such as methanesulfonic acid, trifluoromethanesulfonic acid, ethanesulfonic acid, benzenesulfonic acid and paratoluenesulfonic acid. Among others, the inorganic acids are preferred in order to smoothly bring the reaction mixture into contact with water in the step 2. Particularly preferred is the sulfuric acid.

There is also no particular restriction on the amount of the acid used in the step 2. Generally, the acid is used in an amount of 0.01 to 200 mol per 1 mol of the 3,3,3-trifluoropropynyl metal of the general formula [1]. In particular, it suffices in the step 2a to use the acid in an amount of 0.7 mol or more per 1 mol of the 3,3,3-trifluoropropynyl metal. The amount of the acid used in the step 2a is preferably 0.8 to 100 mol, more preferably 0.9 to 50 mol, per 1 mol of the 3,3,3-trifluoropropynyl metal. In the step 2b, the acid may be used in a catalytic amount of 0.3 mol or less.

Further, it suffices in the step 2 to use water in an amount of 0.03 L or more per per 1 mol of the 3,3,3-trifluoropropynyl metal of the general formula [1]. The amount of water used is preferably 0.04 to 30 L, more preferably 0.05 to 15 L, per 1 mol of the 3,3,3-trifluoropropynyl metal.

In the case where the present step 2 is performed on the reaction mixture (A) obtained by the reaction of the 3,3,3-trifluoropropynyl metal and the trifluoroacetate, it is often the case that the contact of the reaction mixture and the water proceeds in a two-phase system. In such a two-phase system, the reaction mixture can be smoothly brought into contact with the water as desired with the addition of a phase transfer catalyst. Examples of the phase transfer catalyst are: quaternary ammonium salts such as tetramethylammonium chloride, tetramethylammonium bromide, tetra-n-butylammonium chloride, tetra-n-butylammonium bromide, benzyltriethylammonium chloride and methyltri-n-octylammonium chloride; and quaternary phosphonium salts such as tetra-n-butylphosphonium chloride, tetra-n-butylphosphonium bromide and methyltriphenylphosphonium chloride. As a matter of course, the above additive is not necessarily required in the case where the suitable reaction conditions are adopted in the present invention.

In the step 2, the preparation solvent used in the preparation of the 3,3,3-trifluoropropynyl metal or the reaction solvent used in the reaction of the step 1 may be contained in the reaction mixture (A). Alternatively, a part or the whole of the solvent may be removed or replaced with another solvent.

The step 2 may be performed under a neat condition that no solvent is contained in the reaction mixture (A).

It is feasible to perform the step 2 with the use of another solvent (called "contact solvent" as distinguished from the reaction solvent of the step 1) although the reaction mixture (A) obtained in the step 1 as it is can be brought into contact with the water in the presence of the acid. The contact solvent is preferably selected from the examples of the reaction solvent usable in the step 1. Any other solvent may alternatively be used as the contact solvent. Examples of the other solvent are: halogenated solvents such as methylene chloride, chloroform and 1,2-dichloroethane; alcohol solvents such as methanol, ethanol, n-propanol, isopropanol, n-butanol and tert-butanol; and nitrile solvents such as acetonitrile, propionitrile and benzonitrile. Among those listed above and listed as the examples of the reaction solvent usable in the step 1, the aliphatic hydrocarbon solvents, aromatic hydrocarbon solvents, ether solvents and alcohol solvents are preferred. The ether solvents are particularly preferred as the contact solvent. The above-mentioned solvents can be used solely or in combination thereof.

In the step 2, it suffices that the amount of the contact solvent used (in the case where the solvent of the step 1 is contained, the total amount of the solvent) is 0.05 L or more per 1 mol of the 3,3,3-trifluoropropynyl metal of the general formula [1]. The amount of the contact solvent used is preferably 0.1 to 30 L, more preferably 0.2 to 20 L.

It suffices in the step 2 to bring the reaction mixture (A) into contact with water in the presence of the acid at 150° C. or lower. The contact temperature is preferably 120° C. to 10° C., more preferably 100° C. to 20° C., still more preferably 75° C. to 30° C.

Further, it suffices in the step 2 to bring the reaction mixture (A) into contact with water in the presence of the acid for 48 hours or less. The contact time is varied depending on the reaction intermediate (1,1,1,5,5,5-hexafluoro-3-pentyn-2-one or its equivalent) and the contact conditions. It is thus preferable to monitor the progress of the contact by analytical means such as gas chromatography, liquid chromatography or nuclear magnetic resonance, and then, determine the point at which there is seen almost no decrease of the reaction intermediate as the end of the reaction.

After the contact of the step 2, the 1,1,1,5,5,5-hexafluoroacetylacetone hydrate of the general formula [3] is obtained as the target product at a high selectivity and yield by ordinary post-treatment operation for organic synthesis. One example of such ordinary post-treatment operation for organic synthesis is to, in the case where the contact completed solution is separated in two phases, to recover and concentrate the organic phase, cool the concentration residue with the addition of a poor solvent, and then, filter out and dry the thus-formed crystalline precipitate. The post-treatment operation is not however limited to this example. Further, it is feasible in the present invention to recover the reaction solvent, by product and unreacted raw material derived from the step 1 or step 2 by separation of the 1,1,1,5,5,5-hexafluoroacetylacetone hydrate, and then, purify and recycle the recovered reaction solvent, by product or unreacted raw material. In the case where the 1,1,1,5,5,5-hexafluoroacetylacetone hydrate is purified with the use of the poor solvent, it is feasible to recover, purify and recycle the poor solvent in the present invention.

In the 1,1,1,5,5,5-hexafluoroacetylacetone hydrate of the general formula [3], n represents a positive integer. There is no particular restriction on the upper limit of the positive integer n.

In the case where n is 1, the hydrate is in the form of a monohydrate of the following formula.

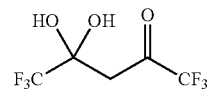

In the case where n is 2, the hydrate is in the form of a dihydrate of the following formula.

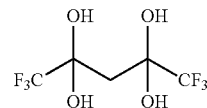

In the case where n is 3 or larger, the hydrate is in the form of having one or more water molecules coordinated on the dihydrate via a hydrogen bond etc. In the case where n is an extremely large integer, it means the dihydrate is present as an aqueous solution. The dihydrate and monohydrate include the case where the hydrate coexists with one water molecule in a state where either or both of carbonyl groups remain (as corresponding to monohydrate form or anhydride form), respectively. Among others, the hydrate where n is 1 or 2 is preferred. Particularly preferred is the hydrate where n is 2.

It is possible to efficiently recover the 1,1,1,5,5,5-hexafluoroacetylacetone hydrate of the general formula [3] from the aqueous phase by extraction with an ether solvent even though the 1,1,1,5,5,5-hexafluoroacetylacetone hydrate has a gem-diol group. As this extraction solvent, there can be used any of the ether solvents listed as the examples of the reaction solvent usable in the step 1. The thus-recovered crude product can be purified to a higher purity level as required by activated carbon treatment, fractional distillation, recrystallization, column chromatography or the like. In particular, the 1,1,1,5,5,5-hexafluoroacetylacetone dihydrate can be isolated as a solid (crystal) and purified by easy operation such as washing with a poor solvent. The 1,1,1,5,5,5-hexafluoroacethyl acetone (anhydride) is obtained at a high yield from the purified hydrate by the subsequent dehydration step (see Japanese Laid-Open Patent Publication No. 2001-187760). In the case where the 1,1,1,5,5,5-hexafluoroacethylacetone dihydrate is purified by washing with the poor solvent, it is feasible to recover the washing water and purify and recycle the poor solvent in the present invention.

As mentioned above, it is also possible to obtain the 1,1,1,5,5,5-hexafluoroacetylacetone hydrate of the general formula [3] at a high yield by bringing 1,1,1,5,5,5-hexafluoro-3-pentyn-2-one trimethylsilylethyl ketal into contact with the water in the presence of the acid (see Example 2). In the present invention, the 1,1,1,5,5,5-hexafluoro-3-pentyn-2-one or its equivalent formed in the step 1 may be contained as such a derivative in the reaction mixture (A). There is no particular restriction on the form of the derivative. The derivative is preferably in the form of being protected by any of hydroxyl protecting groups that can be deprotected upon contact with water in the presence of acid as described in Protective Groups in Organic Synthesis, Third Edition, 1999, John Wiley & Sons, Inc. Particularly preferred is the derivative protected by an acyl group such as formyl, acetyl or benzoyl or a silyl group such as trimethylsilyl, triethylsilyl or dimethyl-tert-butylsilyl.

As mentioned above, the 1,1,1,5,5,5-hexafluoro-3-pentyn-2-one metal hemiketal of the general formula [5] and the 1,1,1,5,5,5-hexafluoro-3-pentyn-2-one hydrate or alkyl hemiketal of the general formula [6] are very important intermediate compounds in the production method of the present invention. As long as the present inventors know, these compounds are novel compounds.

In the 1,1,1,5,5,5-hexafluoro-3-pentyn-2-one metal hemiketal of the general formula [5], M represents a lithium atom or a halogenated magnesium group (MgX); and X represents a chlorine atom, a bromine atom or an iodine atom.

Further, R represents an alkyl group in the 1,1,1,5,5,5-hexafluoro-3-pentyn-2-one metal hemiketal of the general formula [5]. The alkyl group R is derived from and is the same as that of the trifluoroacetate of the general formula [2].

In the 1,1,1,5,5,5-hexafluoro-3-pentyn-2-one hydrate or alkyl hemiketal of the general formula [6], $R^2$ represents a hydrogen atom or an alkyl group. The alkyl group $R^2$ is derived from and is the same as R of the trifluoroacetate of the general formula [2].

[Dehydration Step]

Next, the dehydration step of the 1,1,1,5,5,5-hexafluoroacetylacetone hydrate will be explained below.

The 1,1,1,5,5,5-hexafluoroacetylacetone hydrate of the general formula [3] formed in the step 2 is suitably adaptable to the dehydration step. It is possible by this dehydration step to produce the 1,1,1,5,5,5-hexafluoroacetylacetone of the formula [4] at a high selectivity and yield. The dehydration step can be performed with reference to Japanese Laid-Open Patent Publication No. 2001-187760, No. 2001-261607, No. 2001-354610 and No. 2004-2466, J. Inorganic and Nuclear Chemistry, 1956, vol. 2, p. 11-31, and the like. For example, Japanese Laid-Open Patent Publication No. 2001-187760 discloses a process for dehydrating 1,1,1,5,5,5-hexafluoroacetylacetone dihydrate by the use of concentrated sulfuric acid as a dehydrating agent.

There is no particular restriction on the process for dehydration of the hydrate. For example, it is feasible to perform the dehydration by thermal decomposition, azeotropic dehydration etc. or by the use of a dehydrating agent. Among others, preferred is a dehydration process using a dehydrating agent.

Example of the dehydrating agent are not only concentrated sulfuric acid as disclosed in Japanese Laid-Open Patent Publication No. 2001-187760, but also acetic anhydride, diphosphorus pentoxide, soda lime, calcium chloride, anhydrous zinc chloride, anhydrous magnesium sulfate, anhydrous calcium sulfate, alumina, silica gel and synthetic zeolite.

EXAMPLES

The present invention will be described in more detail below by way of the following examples. It should be understood that the following examples are illustrative and are not intended to limit the present invention thereto. In the following examples, the abbreviations Me and Et refer to methyl and ethyl, respectively.

Example 1

A solution I was prepared by adding 5.1 g (36 mmol, 1.2 eq) of ethyl trifluoroacetate of the following formula to 50 mL of tetrahydrofuran and cooling the resulting mixture to −30° C. while stirring.

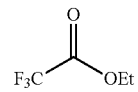

On the other hand, a solution II was prepared by adding 4.0 g (43 mmol, 1.4 eq) of 3,3,3-trifluoropropyne of the following formula to 50 mL of tetrahydrofuran at 0° C., further adding thereto 19 mL (30 mmol, 1.0 eq) of n-butyl lithium/n-hexane solution (1.6 M) at −30° C., and then, stirring the resulting mixture for 15 minutes at the same temperature as above.

The solution I was mixed with the solution II. The mixed solution was stirred at −30° C. for 2 hours (as a reaction completed solution). The operation until this point was performed under a nitrogen atmosphere.

The reaction completed solution was added to 78 g of aqueous sulfuric acid solution (prepared from 15 g (150 mmol, 5.0 eq) of concentrated sulfuric acid and 63 g of ice water) at 0° C. The thus-mixed solution was stirred at 50° C. for 10 hours (in a two-phase system) and separated into two phases. The aqueous layer was extracted with tert-butyl methyl ether. Then, the extract was combined with the organic phase.

The recovered organic phase was subjected to $^{19}$F-NMR quantification by internal standard method (internal standard material: α,α,α-trifluorotoluene). It was confirmed that 25 mmol of 1,1,1,5,5,5-hexafluoroacetylacetone dihydrate of the following formula and 0.60 mmol of 1,1,1,5,5,5-hexafluoroacetylacetone monohydrate of the following formula were contained in the recovered organic phase. The total yield of the target product was 87%.

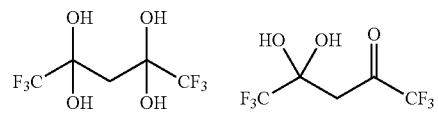 [SMILES: OC(O)(CC(O)(O)C(F)(F)F)C(F)(F)F ; O=C(CC(O)(O)C(F)(F)F)C(F)(F)F]

Further, the recovered organic phase was washed with 20 mL of water and concentrated under a vacuum (40° C./60 mmHg). To the concentration residue, 18 mL of toluene was added. The resulting mixture was stirred for 3 hours and 10 minutes under ice cooling, thereby forming a crystalline precipitate. The crystalline precipitate was filtered out and dried under a vacuum. By this, 4.0 g of 1,1,1,5,5,5-hexafluoroacetone hydrate (dihydrate:monohydrate=97:3) was yielded. The total yield was 53%.

The $^1$H-NMR and $^{19}$F-NMR data of the 1,1,1,5,5,5-hexafluoroacetone dihydrate and monohydrate were as indicated below.

$^1$H-NMR [standard material: $(CH_3)_4Si$, deuterated solvent: $CD_3CN$]

Dihydrate/δ ppm: 6.08 (2H). Four hydroxyl protons was unidentified.

$^{19}$F-NMR [standard material: $CFCl_3$, deuterated solvent: $CD_3CN$]

Dihydrate/δ ppm: −87.78 (6F).

Monohydrate/δ ppm: −80.02 (3F), −86.81 (3F).

To 3.4 g (14 mmol, 1 eq) of the above-obtained 1,1,1,5,5,5-hexafluoroacetone hydrate, 6.8 g (69 mmol, 4.9 eq) of concentrated sulfuric acid was added at 10° C. The resulting mixture was stirred for 3 hours and 35 minutes at room temperature (in a two-phase system). The thus-dehydrated solution was separated into two phases. By this, 2.7 g of 1,1,1,5,5,5-hexafluoroacetylacetone of the following formula was yielded. The recovery rate was 93%.

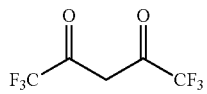

The $^1$H-NMR and $^{19}$F-NMR data of the 1,1,1,5,5,5-hexafluoroacetone were as indicated below.

$^1$H-NMR [standard material: $(CH_3)_4Si$, deuterated solvent: $CD_3CN$]

δ ppm: 10.45 (2H).

$^{19}$F-NMR [standard material: $CFCl_3$, deuterated solvent: $CD_3CN$]

δ ppm: −77.18 (6F).

Example 2

A solution I was prepared by adding 7.1 g (50 mmol, 1.9 eq) of ethyl trifluoroacetate of the following formula to 40 mL of tetrahydrofuran and cooling the resulting mixture to −78° C. while stirring.

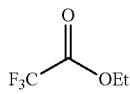

On the other hand, a solution II was prepared by adding 2.5 g (27 mmol, 1.0 eq) of 3,3,3-trifluoropropyne of the following formula to 60 mL of tetrahydrofuran at 0° C., further adding thereto 16 mL (26 mmol, 1.0 eq) of n-butyl lithium/n-hexane solution (1.6 M) at −78° C., and then, stirring the resulting mixture for 30 minutes at the same temperature as above.

The solution I was mixed with the solution II. The mixed solution was stirred at −78° C. for 1 hour (as a reaction mixture solution). The operation until this point was performed under a nitrogen atmosphere.

The reaction mixture solution was added to 21 g of trimethylsilyl chloride tetrahydrofuran solution (prepared from 3.0 g (28 mmol, 1.1 eq) of trimethylsilyl chloride and 18 g of tetrahydrofuran) at 0° C. Then, the reaction mixture solution was stirred for 3 days at room temperature (as a reaction completed solution).

The reaction completed solution was subjected to $^{19}$F-NMR quantification by internal standard method (internal standard material: α,α,α-trifluorotoluene). It was confirmed that 20 mmol of 1,1,1,5,5,5-hexafluoro-3-pentyn-2-one trimethylsilylethyl ketal of the following formula was contained in the reaction completed solution. The total yield of this equivalent compound was 77%.

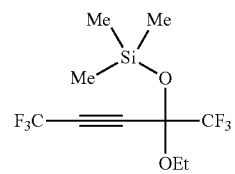

The reaction completed solution was directly concentrated under a vacuum (40° C./200 hPa), thereby forming a precipitate of lithium chloride. The precipitated lithium chloride was removed by decantation. The thus-obtained solution was distillated under a vacuum (46 to 65° C./~2.8 kPa). By this, 4.2 g of 1,1,1,5,5,5-hexafluoro-3-pentyn-2-one trimethylsilylethyl ketal was yielded. The total yield was 54%. The gas chromatographic purity was 97.4%.

The $^1$H-NMR, $^{13}$C-NMR and $^{19}$F-NMR data of the 1,1,1,5,5,5-hexafluoro-3-pentyn-2-one trimethylsilylethyl ketal were as indicated below.

$^1$H-NMR [standard material: $(CH_3)_4Si$, deuterated solvent: $CD_3Cl_3$]

δ ppm: 0.26 (9H), 1.29 (3H), 3.78 (2H).

$^{13}$C-NMR [standard material: $(CH_3)_4Si$, deuterated solvent: $CD_3Cl_3$]

δ ppm: 0.82, 14.78, 61.37, 73.89, 79.53, 91.02, 113.42, 120.57.

$^{19}$F-NMR [standard material: $C_6F_6$, deuterated solvent: $CD_3Cl_3$]

δ ppm: 78.09, 109.95.

To 0.15 g (0.49 mmol, 1 eq) of the above-obtained 1,1,1,5,5,5-hexafluoro-3-pentyn-2-one trimethylsilylethyl ketal, 2.0 mL of tetrahydrofuran and 1.3 g of aqueous sulfuric acid solution (prepared from 0.30 g (3.1 mmol, 6.3 eq) of concentrated sulfuric acid and 1 g of water) were added. The resulting mixture was stirred for 3 hours and 30 minutes at 40° C. and further stirred for 4 hours and 30 minutes at 50° C. (as a uniform solution). The rate of conversion from the 1,1,1,5,5,5-hexafluoro-3-pentyn-2-one trimethylsilylethyl ketal to 1,1,1,5,5,5-hexafluoroacetylacetone dihydrate of the following formula was measured by $^{19}$F-NMR analysis. The conversion rate was 93%.

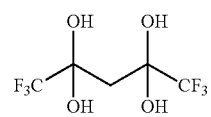

Example 3

First, 6.5 kg (69 mol, 1.0 eq) of 3,3,3-trifluoropropyne of the following formula was added to 36 kg of tert-butyl methyl ether at −98° C. to −44° C., followed by adding thereto 17 kg (66 mol, 1.0 eq) of n-butyl lithium/n-heptane solution (25 wt %) at −103° C. to −28° C.

The resulting mixture was stirred for 30 minutes at −30° C. Further, 9.5 kg (67 mol, 1.0 eq) of ethyl trifluoroacetate of the following formula was added to the mixture at −38° C. to −33° C.

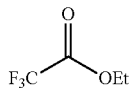

The mixture was then stirred for 2 hours at −30° C. (as a reaction completed solution). The operation until this point was performed under a nitrogen atmosphere.

The reaction completed solution was added to 64 kg of aqueous sulfuric acid solution (prepared from 16 kg (160 mol, 2.4 eq) of concentrated sulfuric acid and 48 kg of water) at 3° C. The thus-mixed solution was stirred for 30 minutes at 5° C. (in a two-phase system) and separated into two phases.

The recovered organic phase was subjected to $^{19}$F-NMR quantification by internal standard method (internal standard material: α,α,α-trifluorotoluene). It was confirmed that 37 mol of 1,1,1,5,5,5-hexafluoro-3-pentyn-2-one ethyl hemiketal of the following formula and 29 mol of 1,1,1,5,5, 5-hexafluoro-3-pentyn-2-one hydrate of the following formula were contained in the recovered organic phase. The total yield of the equivalent product was quantitative.

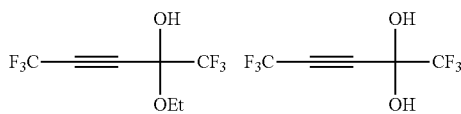

The $^{19}$F-NMR data of the 1,1,1,5,5,5-hexafluoro-3-pentyn-2-one ethyl hemiketal and hydrate were as indicated below.

$^{19}$F-NMR [standard material: CFCl$_3$, deuterated solvent: not used, analysis performed on recovered organic phase as it is]

Ethyl hemiketal/δ ppm: −85.05 (3F), −52.52 (3F).

Hydrate/δ ppm: −86.37 (3F), −52.52 (3F).

To the recovered organic phase, 29 kg of aqueous sulfuric acid solution (prepared from 0.29 kg (3.0 mol, 0.045 eq) of concentrated sulfuric acid and 29 kg of water) was newly added. The resulting mixture was stirred for 10 hours at 52° C. (in a two-phase system) and separated into two phases.

The recovered organic phase was subjected to $^{19}$F-NMR quantification by internal standard method (internal standard material: α,α,α-trifluorotoluene). It was confirmed that 58 mol of 1,1,1,5,5,5-hexafluoroacetylacetone hydrate of the following formula was contained in the recovered organic phase. The total yield of the target product was 88%.

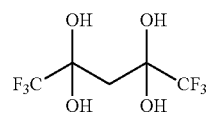

The recovered organic phase was washed with 40 kg of water and concentrated under a vacuum (oil bath temperature: ~29° C., vacuum degree; ~6.2 kPa). To the concentration residue, 30 kg of n-heptane was added. The concentration residue mixture was again concentrated under a vaccum (oil bath temperature: ~33° C., vacuum degree; ~5.5 kPa). Then, 45 kg of n-heptane was added to the concentration residue. The concentration residue mixture was stirred for 2 hours at 4° C., thereby forming a crystalline precipitate. The crystalline precipitate was filtered out and dried under a vacuum. By this, 13 kg of 1,1,1,5,5,5-hexafluoroacetylacetone hydrate (dihydrate:monohydrate=92:8). The total yield was 82%.

To 4.0 kg (41 mol, 2.6 eq) of concentrated sulfuric acid, 4.0 kg (16 mol, 1.0 eq) of the above-obtained 1,1,1,5,5,5-hexafluoroacetylacetone hydrate was added at 15° C. to 20° C. The resulting mixture was stirred for 3 hours and 30 minutes at the same temperature as above (in a two-phase system).

The thus-dehydrated solution was separated into two phases. By this, 3.3 kg of 1,1,1,5,5,5-hexafluoroacetylacetone of the following formula was yielded as a crude product. The recovery rate was quantitative. The gas chromatographic purity of the crude product was 99.7%.

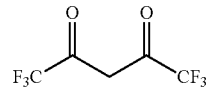

Subsequently, 3.2 kg of the crude product was mixed with 0.33 kg (3.4 mol, 0.23 eq) of concentrated sulfuric acid and then subjected to fractional distillation (distillation temperature: 69° C./atmospheric pressure). By this, 2.6 kg of 1,1,1, 5,5,5-hexafluoroacetylacetone of the above formula was yielded as a purified product. The recovery rate was 81%. The gas chromatographic purity of the purified product was 100%.

Example 4

A solution I was prepared by adding 9.2 g (65 mmol, 1.6 eq) of ethyl trifluoroacetate of the following formula to 35 mL of tetrahydrofuran and cooling the resulting mixture to −40° C. while stirring.

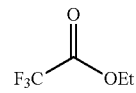

On the other hand, a solution II was prepared by adding 4.0 g (43 mmol, 1.1 eq) of 3,3,3-trifluoropropyne of the following formula to 35 mL of tetrahydrofuran at 0° C., further adding thereto 20 mL (40 mmol, 1.0 eq) of methyl magnesium chloride/tetrahydrofuran solution (2.0 M) at 0° C., and then, stirring the resulting mixture for 30 minutes at the same temperature as above.

The solution I was mixed with the solution II. The mixed solution was stirred at −30° C. for 1 hour and 10 minutes (as a reaction completed solution). The operation until this point was performed under a nitrogen atmosphere.

The reaction completed solution was added to 100 g of aqueous sulfuric acid solution (prepared from 20 g (200 mmol, 5.0 eq) of concentrated sulfuric acid and 84 g of ice water) at 0° C. The thus-mixed solution was stirred at 50° C. for 1 hour and 10 minutes (in a two-phase system) and separated into two phases. The aqueous layer was extracted with tert-butyl methyl ether. Then, the extract was combined with the organic phase.

The recovered organic phase was subjected to $^{19}$F-NMR quantification by internal standard method (internal standard material: α,α,α-trifluorotoluene). It was confirmed that 1,1,1,5,5,5-hexafluoroacetylacetone dihydrate of the following formula and 1,1,1,5,5,5-hexafluoroacetylacetone monohydrate of the following formula were contained in a total amount of 14 mmol in the recovered organic phase. The total yield of the target product was 35%.

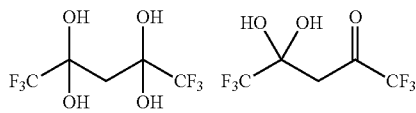

Example 5

First, 12 g (130 mmol, 1.1 eq) of 3,3,3-trifluoropropyne was added to 90 mL of tert-butyl methyl ether at −49° C. to −50° C., followed by adding thereto 31 g (120 mmol, 1.0 eq) of n-butyl lithium/n-heptane solution (25 wt %) at −56° C. to −26° C.

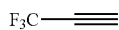

The resulting mixture was stirred for 35 minutes at −30° C. Further, 16 g (120 mmol, 1.0 eq) of methyl trifluoroacetate of the following formula was added to the mixture at −45° C. to −40° C.

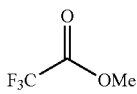

The mixture was then stirred for 2 hours at −30° C. (as a reaction completed solution). The operation until this point was performed under a nitrogen atmosphere.

The reaction completed solution was added to 117 g of aqueous sulfuric acid solution (prepared from 29 g (300 mmol, 2.5 eq) of concentrated sulfuric acid and 88 g of water) at 5° C. The thus-mixed solution was stirred for 15 minutes at the same temperature as above (in a two-phase system) and separated into two phases.

The recovered organic phase was subjected to $^{19}$F-NMR quantification by internal standard method (internal standard material: α,α,α-trifluorotoluene). It was confirmed that 1,1,1,5,5,5-hexafluoro-3-pentyn-2-one methyl hemiketal of the following formula and 1,1,1,5,5,5-hexafluoro-3-pentyn-2-one hydrate of the following formula were contained in a total amount of 120 mmol in the recovered organic phase. The total yield of the equivalent product was quantitative.

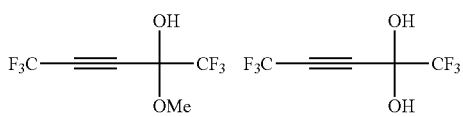

The $^{19}$F-NMR data of the 1,1,1,5,5,5-hexafluoro-3-pentyn-2-one methyl hemiketal was as indicated below.

$^{19}$F-NMR [standard material: $CFCl_3$, deuterated solvent: not used, analysis performed on recovered organic phase as it is]

δ ppm: −84.15 (3F), −51.76 (3F).

To the recovered organic phase, 60 g of aqueous sulfuric acid solution (prepared from 0.60 g (6.1 mmol, 0.051 eq) of concentrated sulfuric acid and 59 g of water) and 42 mL of tert-butyl methyl ether were newly added. The resulting mixture was stirred for 15 hours at 49° C. (in a two-phase system) and separated into two phases.

The recovered organic phase was subjected to $^{19}$F-NMR quantification by internal standard method (internal standard material: α,α,α-trifluorotoluene). It was confirmed that 99 mmol of 1,1,1,5,5,5-hexafluoroacetylacetone hydrate of the following formula was contained in the recovered organic phase. The total yield of the target product was 83%.

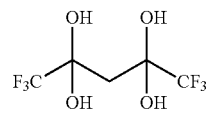 [SMILES: OC(O)(CC(O)(O)C(F)(F)F)C(F)(F)F]

Example 6

To 2109 g of the distillate obtained by vacuum concentration in Example 3, 26.4 g of 33% aqueous sodium hydroxide solution (prepared from 8.8 g (220 mmol) of sodium hydroxide and 17.6 g of water) was added. The thus-obtained solution was subjected to fractional distillation (theoretical plate number: 10). By this, 887.6 g of tert-butyl methyl ether (distillation temperature: ~62° C., atmospheric pressure) and 726.9 g of n-heptane (distillation temperature: ~99° C., atmospheric pressure) were recovered.

Then, 16.0 g (170 mmol, 1.1 eq) of 3,3,3-trifluoropropyne of the following formula was added to 120 mL of the recovered tert-butyl methyl ether at −51° C. to −38° C., followed by adding thereto 41.0 g (160 mmol, 1.0 eq) of n-butyl lithium/n-heptane solution (25 wt %) at −51° C. to −29° C.

The resulting mixture was stirred for 30 minutes at −30° C. Further, 23.9 g (168 mmol, 1.1 eq) of ethyl trifluoroacetate of the following formula was added to the mixture at −42° C. to −39° C.

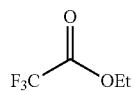

The mixture was then stirred for 2 hours at −30° C. (as a reaction completed solution). The operation until this point was performed under a nitrogen atmosphere.

The reaction completed solution was added to 157.2 g of aqueous sulfuric acid solution (prepared from 39.2 g (400 mmol, 2.5 eq) of concentrated sulfuric acid and 118 g of water) at 3° C. The thus-mixed solution was stirred for 10 minutes at 5° C. (in a two-phase system) and separated into two phases.

The recovered organic phase was subjected to $^{19}$F-NMR quantification by internal standard method (internal standard material: α,α,α-trifluorotoluene). It was confirmed that 55 mmol of 1,1,1,5,5,5-hexafluoro-3-pentyn-2-one ethyl hemiketal of the following formula and 70 mmol of 1,1,1,5,5,5-hexafluoro-3-pentyn-2-one hydrate of the following formula were contained in the recovered organic phase. The total yield of the equivalent product was 79%.

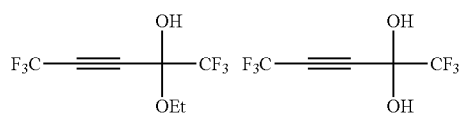 [SMILES: CCOC(O)(C#CC(F)(F)F)C(F)(F)F ; OC(O)(C#CC(F)(F)F)C(F)(F)F]

It has been shown by the above results that it was possible to properly recycle the recovered solvent.

Comparative Example 1

First, 8.0 g (85 mmol, 1.1 eq) of 3,3,3-trifluoropropyne was added to 60 mL of tert-butyl methyl ether at −40° C. to −38° C., followed by adding thereto 50 mL (80 mmol, 1.0 eq) of n-butyl lithium/n-hexane solution (1.6 M) at −40° C. to −25° C.

The resulting mixture was stirred for 1 hour and 5 minutes at −30° C. Further, 56 g of ethyl trifluoroacetate/tert-butyl methyl ether solution (prepared from 12 g (84 mmol, 1.1 eq) of ethyl trifluoroacetate and 44 g of tert-butyl methyl ether) was added to the mixture at −30° C.

The mixture was then stirred for 2 hours at the same temperature as above (as a reaction completed solution). The operation until this point was performed under a nitrogen atmosphere.

The reaction completed solution was added to 80 mL of water under ice cooling, stirred for 10 hours at 50° C. (in a two-phase system) and separated into two phases.

The recovered organic phase was subjected to $^{19}$F-NMR quantification by internal standard method (internal standard material: α,α,α-trifluorotoluene). It was confirmed that 1,1,1,5,5,5-hexafluoroacetylacetone dihydrate of the following formula and 1,1,1,5,5,5-hexafluoroacetylacetone monohydrate of the following formula were contained in a total amount of only 1.3 mmol in the recovered organic phase. The total yield of the hydrate product was 2%.

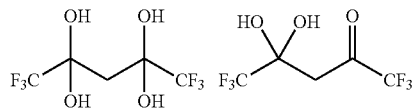 [SMILES: OC(O)(CC(O)(O)C(F)(F)F)C(F)(F)F ; O=C(CC(O)(O)C(F)(F)F)C(F)(F)F]

INDUSTRIAL APPLICABILITY

The 1,1,1,5,5,5-hexafluoroacetylacetone produced by the present invention is usable as intermediates for pharmaceutical and agrichemical products and electronic materials.

The invention claimed is:

1. A method for producing a 1,1,1,5,5,5-hexafluoroacetylacetone hydrate of the general formula [3]:

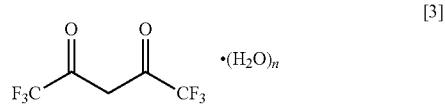

where n represents a positive integer,
the method comprising:
step 1: obtaining a reaction mixture (A) that contains at least 1,1,1,5,5,5-hexafluoro-3-pentyn-2-one or an equivalent thereof by reaction of a 3,3,3-trifluoropropynyl metal of the general formula [1] with a trifluoroacetate of the general formula [2]:

where M represents a lithium atom or a halogenated magnesium group (MgX); and X represents a chlorine atom, a bromine atom or an iodine atom;

where R represents an alkyl group; and
step 2: forming the 1,1,1,5,5,5-hexafluoroacetylacetone hydrate of the general formula [3] by contact of the reaction mixture (A) obtained in the step 1 with water in the presence of an acid.

2. The method according to claim 1, further comprising: purifying the 1,1,1,5,5,5-hexafluoroacetylacetone hydrate formed in the step 2.

3. The method according to claim 2, wherein the reaction of the step 1 is performed with the use of a reaction solvent.

4. The method according to claim 3, further comprising: recycling at least one of the reaction solvent and raw substrate material separated from the 1,1,1,5,5,5-hexafluoroacetylacetone hydrate; and.

5. The method according to claim 1, wherein the equivalent of the 1,1,1,5,5,5-hexafluoro-3-pentyn-2-one is a 1,1,1,5,5,5-hexafluoro-3-pentyn-2-one metal hemiketal of the general formula [5]:

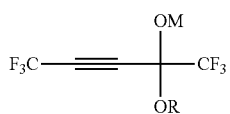

[5]

where M is a lithium atom or a halogenated magnesium group (MgX); X represents a chlorine atom, a bromine atom or an iodine atom; and R represents an alkyl group.

6. The method according to claim 1, wherein the equivalent of the 1,1,1,5,5,5-hexafluoro-3-pentyn-2-one is a 1,1,1,5,5,5-hexafluoro-3-pentyn-2-one hydrate or alkyl hemiketal of the general formula [6]:

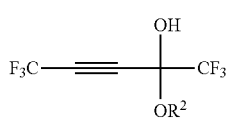

[6]

where $R^2$ represents a hydrogen atom or an alkyl group.

7. The method according to claim 1, wherein M of the 3,3,3-trifluoropropyl metal of the general formula [1] is a lithium atom.

8. The method according to claim 1, wherein the acid is sulfuric acid.

9. The method according to claim 1, wherein step 1 comprises: obtaining a preparation solution (B) by reaction of 3,3,3-trifluoropropyne of the formula [7] with an organic lithium reagent or Grignard reagent of the general formula [8] in a preparation solvent, and then, obtaining a reaction mixture (C) as the reaction mixture (A) by reaction of the preparation solution (B) with the trifluoroacetate of the general formula [2]:

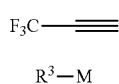

[7]

$R^3$—M

[8]

where $R^3$ represents a $C_1$-$C_8$ straight or branched or $C_3$-$C_8$ cyclic alkyl group; M represents a lithium atom or a halogenated magnesium group (MgX); and X represents a chlorine atom, a bromine atom or an iodine atom.

10. The method according to claim 9, further comprising: purifying the 1,1,1,5,5,5-hexafluoroacetylacetone hydrate formed in the step 2 to a higher purity level.

11. The method according to claim 10, further comprising: purifying and recycling at least one of the preparation solution and raw substrate material separated from the 1,1,1,5,5,5-hexafluoroacetylacetone hydrate.

12. A method for producing 1,1,1,5,5,5-hexafluoroacetylacetone of the formula [4]:

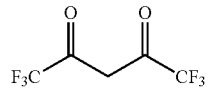

[4]

the method comprising:
producing a 1,1,1,5,5,5-hexafluoroacetylacetone hydrate by the method according to claim 1; and
dehydrating the 1,1,1,5,5,5-hexafluoroacetylacetone hydrate.

13. A 1,1,1,5,5,5-hexafluoro-3-pentyn-2-one metal hemiketal of the general formula [5]:

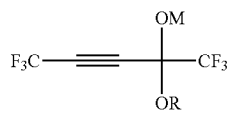

[5]

where M represents a lithium atom or a halogenated magnesium group (MgX); X represents a chlorine atom, a bromine atom or an iodine atom; and R represents an alkyl group.

14. A 1,1,1,5,5,5-hexafluoro-3-pentyn-2-one hydrate or alkyl hemiketal of the general formula [6]:

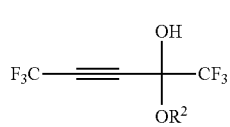

[6]

where $R^2$ represents a hydrogen atom or an alkyl group.

* * * * *